US005254110A

United States Patent [19]

Marcus et al.

[11] Patent Number: 5,254,110

[45] Date of Patent: Oct. 19, 1993

[54] VACUUM SYSTEM FOR USE DURING SURGICAL PROCEDURES

[76] Inventors: Donald H. Marcus, 16837 Calahan St., Sepulveda, Calif. 91343; Edward J. Hunter, 8415 Oakdale Ave., Canoga Park, Calif. 91306

[21] Appl. No.: 896,113

[22] Filed: Jun. 9, 1992

[51] Int. Cl.[5] .................... A61M 1/00

[52] U.S. Cl. .................... 604/322; 128/DIG. 26; 24/570; 248/68.1

[58] Field of Search .................... 24/30.5 L, 30.5 P, 543, 24/570; 248/56, 65, 68.1, 75; 128/DIG. 26; 604/19, 322, 174

[56] References Cited

U.S. PATENT DOCUMENTS

| | | | |
|---|---|---|---|
| 2,913,740 | 11/1959 | Eldridge | 248/68.1 |
| 3,210,816 | 10/1965 | Clemons | 128/852 |
| 3,338,538 | 8/1967 | Roche | 128/DIG. 26 |
| 3,374,509 | 3/1968 | Logan et al. | 24/570 |
| 3,682,180 | 8/1972 | McFarlane | 604/174 |
| 3,702,612 | 11/1972 | Schlesinger | 128/DIG. 26 |
| 4,606,735 | 8/1986 | Wilder et al. | 604/180 |
| 4,773,768 | 9/1988 | Leeper | 604/322 |
| 4,795,429 | 1/1989 | Feldstein | 604/80 |
| 4,955,864 | 9/1990 | Hajduch | 604/174 |
| 4,988,062 | 1/1991 | London | 248/68.1 |
| 5,054,723 | 10/1991 | Arnold | 248/65 |

*Primary Examiner*—C. Fred Rosenbaum
*Assistant Examiner*—Michael Rafa
*Attorney, Agent, or Firm*—Kelly, Bauersfeld & Lowry

[57] ABSTRACT

A surgical aspiration system includes aspirating equipment having an inlet through which a vacuum may be drawn for collecting bodily fluids during a surgical procedure. Suction tubing is connected to the aspirating equipment inlet and extends therefrom to a patient undergoing the surgical procedure. A suction catheter is attached to a distal end of the suction tubing for positioning within a portion of the patient's upper airway. A support for the suction tubing includes a normally horizontally disposed base which is adapted to fit beneath a patient-supporting mattress, and a bracket member extending vertically upwardly from the base. An aperture is provided through the bracket member in which a portion of the suction tubing is positioned. A pair of anchor slots are provided in the bracket member adjacent to the aperture, for pinching off a portion of the distal end of the surgical tubing to essentially stop the flow of fluid through the suction tubing. The aperture is constructed to include inwardly disposed teeth which permit insertion of the suction tubing into the aperture, but prevent withdrawal of the suction tubing from the aperture without destroying the utility of the suction tubing.

9 Claims, 1 Drawing Sheet

VACUUM SYSTEM FOR USE DURING SURGICAL PROCEDURES

BACKGROUND OF THE INVENTION

This invention relates generally to aspirating equipment utilized during surgical procedures. More specifically, the present invention relates to a support for suction tubing forming a portion of a surgical aspiration system.

In the U.S. alone there are millions of surgical procedures performed annually. A majority of surgical procedures require the use of an endotracheal tube to ensure a patent airway during the perioperative, operative and post operative periods. Most often the endotracheal tube is removed in the operating room as the patient emerges from anesthesia. To ensure that the patient does not aspirate unwanted material such as blood, mucus, stomach contents or other foreign material into the lower respiratory tract (any structures proximal to the vocal cords), it is imperative that a reliable and readily available method of airway aspiration be present.

In operating rooms, intensive care units and emergency rooms, the ability to aspirate and remove bodily fluids is of paramount importance. During the induction and emergence from general anesthesia, as well as other altered states of consciousness, a patient is at an increased risk to aspirate stomach contents, blood or other foreign material into the lungs. Typically a vacuum system is provided to minimize the risk that a patient will aspirate such fluids.

In a typical operating room the vacuum system is connected to aspirating equipment including a vacuum canister provided for collection and disposal of aspirated bodily fluids. Suction tubing is connected to an inlet to the vacuum canister and extends to the patient. The distal end of the suction tubing is attached to the proximal end of a suction catheter which is configured for insertion into the upper airway of the patient. When not in use, the suction catheter is often either stuffed into a section of an anesthesia machine, placed under the patient mattress, or left dangling from a wall or in another location that is inaccessible when needed. Too often the suction tubing and catheter are left to fall on the floor of the operating room.

Additionally, in use the typical vacuum system is left on during the perioperative and through the postoperative period. The distal end of the suction catheter typically has one or more apertures which, due to the air being drawn therethrough, creates a noticeable, bothersome hissing sound that is stopped by pinching the suction tubing or catheter themselves, or by turning off the vacuum system completely. Obviously, if the system is turned off it is not available for immediate use. However, there has been no prior satisfactory means whereby operating room personnel could properly position the suction catheter adjacent to the patient and, simultaneously, pinch off the tubing or catheter to stop the flow of air therethrough and minimize the hissing sound.

Accordingly, there has been a need for a novel vacuum system for use during surgical procedures, which is capable of properly positioning the suction tubing and catheter adjacent to a patient in a reliable and safe manner. The components of the vacuum system should all be easy to manufacture, relatively inexpensive, and adaptable for use with the standard vacuum systems provided in typical medical care facilities. Moreover, each of the components of the vacuum system having any contact whatsoever with patient bodily fluids must be disposable. Further, there is a need for a support for suction tubing forming a portion of a surgical aspiration system, having a construction allowing convenient placement adjacent to a patient, preferably on or near the operating table, capable of having suction tubing securely held therein, but which prevents removal of the suction tubing therefrom. Moreover, such a support should provide convenient means for pinching off the suction tubing, as desired, to minimize the hissing sound of air being drawn through the suction catheter. The present invention fulfills these needs and provides other related advantages.

SUMMARY OF THE INVENTION

The present invention resides is an improved vacuum system for use during surgical procedures which is adaptable for use with standard aspirating suction tubing and is capable of supporting the distal end of such tubing adjacent to the head of a patient in a reliable and convenient manner for an anesthesia caregiver. The vacuum system comprises, generally, means for drawing a vacuum and aspirating equipment means connectable to the vacuum means and having an inlet through which a vacuum may be drawn, for collecting bodily fluids during a surgical procedure. Suction tubing is connected to the aspirating equipment means inlet and extends therefrom generally to a patient undergoing the surgical procedure. A suction catheter, intended to be positioned within a portion of the patient's upper airway, is attached to a distal end of the suction tubing. Additionally, a support is provided for the suction tubing in order to ensure that the suction tubing, via the suction catheter, is readily available is when needed during the surgical procedure.

In a preferred form of the invention, the support for the suction tubing includes a normally horizontally disposed base which is generally flat and adapted to fit beneath a patient-supporting mattress. A bracket member extends vertically upwardly from the base and is integrally formed with and rigidly positioned with respect to the base.

An aperture is provided through the bracket member, and includes means for permitting insertion of the suction tubing into the aperture, but preventing withdrawal of the suction tubing from the aperture without destroying the utility of the suction tubing. The means for permitting insertion of the suction tubing into the aperture, but preventing withdrawal of the suction tubing therefrom, includes teeth which extend from the bracket member into the aperture. The teeth are configured to permit movement of the suction tubing within the aperture in one direction, but engage the suction tubing to prevent movement in another direction without rendering the suction tubing unusable.

Means are also provided in the bracket member generally adjacent to the aperture, for temporarily anchoring a distal end of the surgical tubing. The anchoring means includes means for pinching off a portion of the distal end of the surgical tubing to essentially stop the flow of fluid through the suction tubing when desired by the anesthesia caregiver. In this regard, the anchoring means includes a pair of vertically extending anchor slots situated adjacent to the aperture.

Other features and advantages of the present invention will be become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
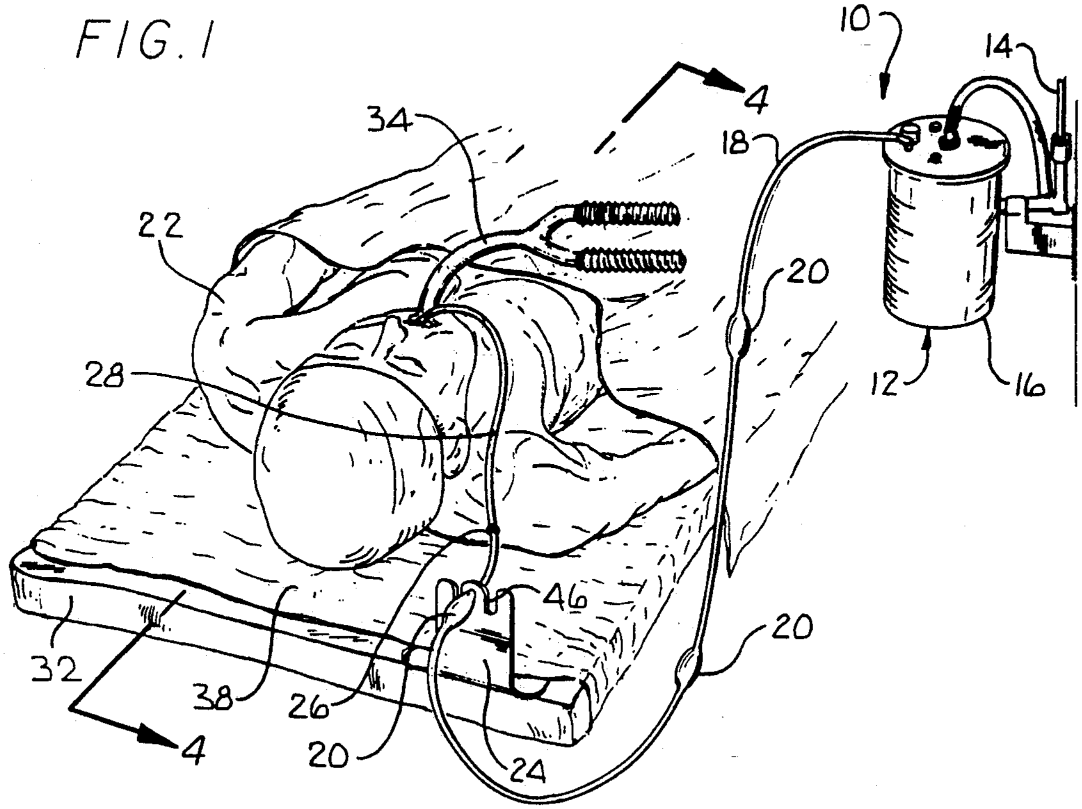
FIG. 1 is a perspective view of a vacuum system for use during surgical procedures embodying the invention, showing the use thereof in a typical surgical environment, wherein the system includes a support for suction tubing partially positioned between an operating table and a patient mattress.
Figure 3:
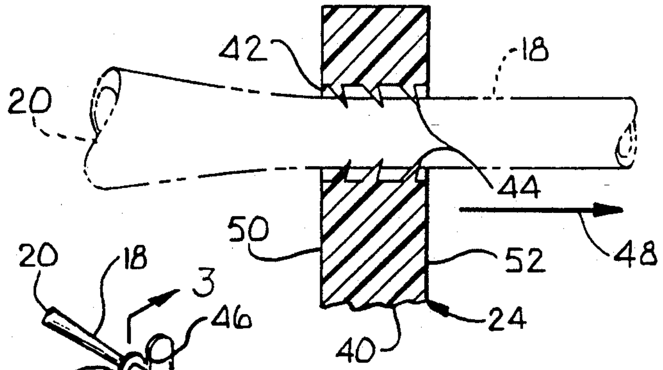
FIG. 3 is an enlarged, fragmented sectional view taken generally along the line 3—3 of FIG. 2, illustrating the manner in which teeth provided within an aperture of the suction tubing support permit the tubing to be pulled in one direction through the aperture, but prevent withdrawal of the tubing therefrom without destroying the tubing and rendering it unusable.
Figure 2:
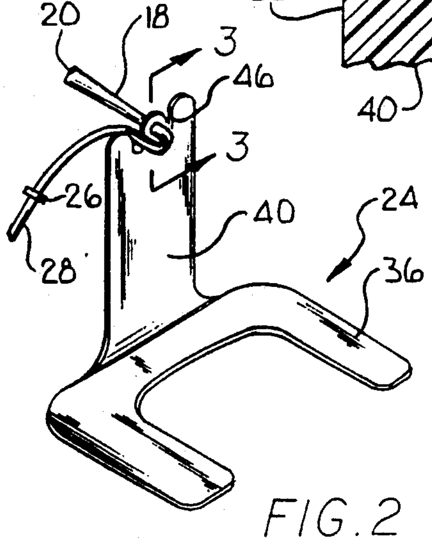
FIG. 2 is front, top and right side perspective view of the support for suction tubing forming a portion of the surgical aspiration system illustrated in FIG. 1, showing the manner in which a distal end of the suction tubing can be positioned within an anchor slot to pinch off a portion of the surgical tubing in order to prevent or severely limit the flow of fluid therethrough.

As shown in the drawings for purposes of illustration, the present invention is concerned with a vacuum system for use during surgical procedures, generally designed in FIG. 1 by the reference number 10. The vacuum system 10 comprises aspirating equipment 12 connectable to a vacuum line 14 provided in most modern operating rooms. The aspirating equipment 12 includes a vacuum canister 16 which receives blood, tissue, vomitus, etc., within a disposable liner, for disposal following the surgical procedure. The vacuum canister 16 includes an inlet to which suction tubing 18 is connected.

Figure 4:
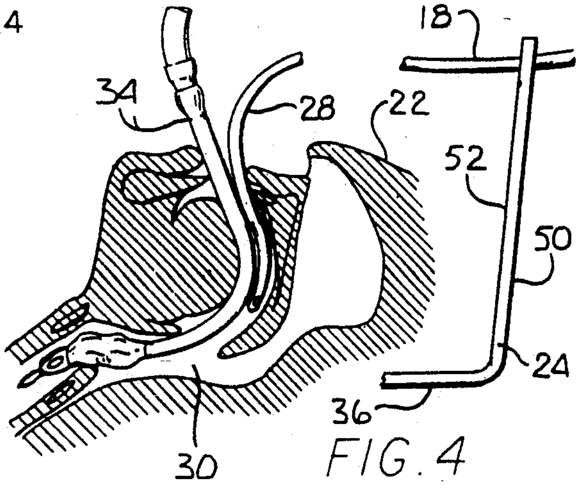
FIG. 4 is an enlarged, fragmented and partially sectional view taken generally along the line 4—4 of FIG. 1, illustrating the positioning of an endotracheal tube and the suction catheter in the patient's airway.

The suction tubing 18 is preferably of the variety having enlarged portions 20 approximately every three feet. The suction tubing 18 extends from the inlet of the vacuum canister 16 toward the patient 22, and a distal end of the suction tubing 18 is inserted through a support 24. A connector 26 permits a suction catheter 28 to be connected to the extreme distal end of the suction tubing 18. The suction catheter 28 is typically positioned within a portion of the patient's upper airway 30 (FIG. 4).

As shown in FIG. 1, the patient 22 is shown lying upon an exemplary operating table 32. An endotracheal tube and suction/aspiration line and catheter 34 is shown extending toward the patient and through the patient's mouth into the patient airway 30. The illustrations in FIGS. 1 and 4 show typical positioning of the endotracheal line and catheter 34 during a surgical operation. The suction catheter 28 is inserted into the upper airway 30 adjacent to the endotracheal catheter 34 as shown.

In accordance with the present invention and as illustrated in FIGS. 1-4, the support 24 for the suction tubing 18, 28 includes a normally horizontally disposed, U-shaped base 36 which is generally flat and adapted to fit beneath a patient-supporting mattress 38. A bracket member 40 extends vertically upwardly from the base 36. The bracket member 40 is preferably integrally formed with an rigidly positioned with respect to the base 36.

An aperture 42 is provided through the bracket member 40, and the distal end of the suction tubing 18 is passed through the aperture 42 as shown. The bracket member 40 includes means for permitting insertion of the distal end of the suction tubing 18 into the aperture 42, but which prevents withdrawal of the suction tubing 18 from the aperture 42 without destroying the utility of the suction tubing. More particularly, the bracket member 40 includes teeth 44 (FIG. 3) which extend inwardly into the aperture 42. The teeth 44 are configured to permit movement of the suction tubing 18 in one direction through the aperture 42, but engage the suction tubing to prevent movement in another direction therethrough without rendering the suction tubing unusable. This helps to ensure that a section of suction tubing 18, when once used during a surgical procedure, will not be inadvertently reused in a subsequent surgical procedure.

A pair of vertically extending anchor slots 46 are provided adjacent to the aperture 42. The anchor slots 46 provide means for temporarily anchoring the distal end of the suction tubing 18 in a convenient and accessible location for the anesthesia caregiver. The anchor slots 46 are configured to permit the distal end of the suction tubing 18 to be twisted and placed therein, to pinch off the fluid passageway within the suction tubing and essentially stop the flow of fluid therethrough.

In use, when preparing the patient 22 and/or the operating room for a surgical procedure, the distal end of the suction tubing 18 is inserted through the aperture 42 provided in the bracket member 40, in the direction indicated by the arrow 48. Preferably the suction tubing 18 is inserted as far as possible, or until further insertion is prevented by engagement between the first enlarged portion 20 of the surgical tubing 18 and a rear wall 50 of the bracket member 40. The extreme distal end of the suction tubing 18 is then connected to the suction catheter 28 utilizing the connector 26.

When the vacuum system 10 is operational, fluid is constantly being drawn through the suction catheter and suction tubing, often resulting in a loud hissing sound which can be irritating to operating room personnel. This hissing sound can be reduced and, in some cases, altogether eliminated by pinching off a portion of the suction tubing 18. This is conveniently accomplished utilizing the support 24 of the present invention by twisting the portion of the suction tubing 18 extending outwardly from the front wall 52 of the bracket member 40, and then folding it back and inserting that portion into one of the anchor slots 46.

At the conclusion of the surgical procedure, consistent with good medical practices, any portion of any apparatus having contact with bodily fluids must either be easily sterilizable or disposable. Since suction tubing 18 is not considered conveniently sterilizable it must be disposed of, together with the suction catheter 28 and any other portions of the vacuum system 10 having contact with bodily fluids. The support 24 helps to ensure that the suction tubing 18 will not be reused inadvertently, due to the configuration of the teeth 44 within the aperture 42, which prevent withdrawal of the suction tubing from the aperture without destroying the utility of the suction tubing.

From the foregoing it is to be appreciated that the improved vacuum system 10 of the present invention advantageously provides means whereby the distal end of surgical tubing 18 and the suction catheter 28 can be positioned and maintained adjacent to the head of a patient 22 undergoing surgery. The support 24 can be economically produced and is simple to utilize in connection with standard aspirating equipment. Moreover, the support 24 provides a convenient means for pinching off the vacuum airway through the suction tubing 18, and helps to ensure that the suction tubing will not be inadvertently reutilized in a subsequent surgical procedure.

Although a particular embodiment of the invention has been described in detail for purposes of illustration, various modifications may be made without departing from the spirit and scope of the invention. Accordingly, the invention is not to be limited, except as by the appended claims.

We claim:

1. A support for suction tubing forming a portion of a surgical aspiration system, the support comprising:

a flat, horizontally disposed base adapted to fit beneath a patient-supporting mattress;

a bracket member extending vertically upwardly from the base, wherein the bracket member is integrally formed and rigidly positioned with respect to the base;

an aperture through the bracket member in which a portion of the suction tubing is positioned;

a pair of vertically extending anchor slots adjacent to the aperture, providing means for temporarily anchoring a distal end of the suction tubing; and means for permitting insertion of the suction tubing into the aperture, but preventing withdrawal of the suction tubing from the aperture without destroying the utility of the suction tubing.

2. A support for suction tubing as set forth in claim 1, wherein the anchoring means includes means for pinching off a portion of the distal end of the surgical tubing to essentially stop the flow of fluid through the suction tubing.

3. A support for suction tubing as set forth in claim 1, wherein the means for permitting insertion of the suction tubing into the aperture, but preventing withdrawal of the suction tubing from the aperture without destroying the utility of the suction tubing, includes teeth extending from the bracket member into the aperture, which teeth permit movement of the suction tubing in one direction through the aperture, but which engage the suction tubing to prevent movement in another direction through the aperture without rendering the suction tubing unusable.

4. A vacuum system for use during surgical procedures, comprising:

means for drawing a vacuum;

aspirating equipment means connectable to the vacuum means and having an inlet through which a vacuum may be drawn, for collecting bodily fluids during a surgical procedure;

suction tubing connected to the aspirating equipment means inlet and extending therefrom to a patient undergoing the surgical procedure;

a suction catheter attached to a distal end of the suction tubing, wherein the suction catheter is intended to be positioned within a portion of the patient's upper airway; and a support for the suction tubing, including:

a flat, horizontally disposed base adapted to fit beneath a patient-supporting mattress;

a bracket member extending vertically upwardly from the base, wherein the bracket member is integrally formed and rigidly positioned with respect to the base;

an aperture through the bracket member in which a portion of the suction tubing is positioned;

means for permitting insertion of the suction tubing into the aperture, but preventing withdrawal of the suction tubing from the aperture without destroying the utility of the suction tubing; and a pair of vertically extending anchor slots adjacent to the aperture, providing means for temporarily anchoring a distal end of the suction tubing.

5. A vacuum system as set forth in claim 4, wherein the anchoring means includes means for pinching off a portion of the distal end of the surgical tubing to essentially stop the flow of fluid through the suction tubing.

6. A vacuum system as set forth in claim 4, wherein the means for permitting insertion of the suction tubing into the aperture, but preventing withdrawal of the suction tubing from the aperture without destroying the utility of the suction tubing, includes teeth extending from the bracket member into the aperture, which teeth permit movement of the suction tubing in one direction through the aperture, but which engage the suction tubing to prevent movement in another direction through the aperture without rendering the suction tubing unusable.

7. A vacuum system for use during surgical procedures, comprising:

means for drawing a vacuum;

aspirating equipment means connectable to a vacuum means and having an inlet through which a vacuum may be drawn, for collecting bodily fluids during a surgical procedure;

suction tubing connected to the aspirating equipment means inlet and extending therefrom generally to a patient undergoing the surgical procedure, the suction tubing having intermittent enlarged portions;

a suction catheter attached to a distal end of the suction tubing, wherein the suction catheter is intended to be positioned within a portion of the patient's upper airway; and a support for the suction tubing, including:

a horizontally disposed base having a flat configuration and adapted to fit beneath a patient-supporting mattress;

a bracket member extending vertically upwardly from the base and being integrally formed with and rigidly positioned with respect to the base;

an aperture through the bracket member in which a portion of the suction tubing is positioned;

means for permitting insertion of the suction tubing into the aperture, but preventing withdrawal of the suction tubing from the aperture without destroying the utility of the suction tubing; and means provided in the bracket member adjacent to the aperture, for temporarily anchoring a distal end of the suction tubing.

8. A vacuum system as set forth in claim 7, wherein the anchoring means includes a pair of vertically extending anchor slots adjacent to the aperture.

9. A vacuum system as set forth in claim 7, wherein the means for permitting insertion of the suction tubing into the aperture, but preventing withdrawal of the suction tubing from the aperture without destroying the utility of the suction tubing, includes teeth extending from the bracket member into the aperture, which teeth permit movement of the suction tubing in one direction through the aperture, but which engage the suction tubing to prevent movement in another direction through the aperture without rendering the suction tubing unusable.

* * * * *